United States Patent
Solitro et al.

(10) Patent No.: US 11,607,274 B2
(45) Date of Patent: Mar. 21, 2023

(54) TOOL AND METHOD TO EVALUATE SAFETY AND ANGULAR RANGES OF PINS AND SCREWS USED FOR PELVIC FIXATION

(71) Applicant: Board of Supervisors of Louisiana State University and Agricultural and Mechanical College, Baton Rouge, LA (US)

(72) Inventors: Giovanni Francesco Solitro, Shreveport, LA (US); Massimo Morandi, Bloomfield Hills, MI (US); R. Shane Barton, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 401 days.

(21) Appl. No.: 16/799,804

(22) Filed: Feb. 24, 2020

(65) Prior Publication Data
US 2020/0268449 A1  Aug. 27, 2020

Related U.S. Application Data

(60) Provisional application No. 62/809,183, filed on Feb. 22, 2019.

(51) Int. Cl.
| A61B 34/10 | (2016.01) |
| A61B 17/86 | (2006.01) |
| A61B 6/03 | (2006.01) |
| G16H 20/40 | (2018.01) |
| A61B 17/00 | (2006.01) |

(52) U.S. Cl.
CPC .............. *A61B 34/10* (2016.02); *A61B 6/032* (2013.01); *A61B 17/86* (2013.01); *G16H 20/40* (2018.01); *A61B 2017/00199* (2013.01); *A61B 2017/00221* (2013.01); *A61B 2034/104* (2016.02); *A61B 2034/105* (2016.02); *A61B 2034/108* (2016.02)

(58) Field of Classification Search
CPC ... A61B 17/86; A61B 17/8605; A61B 17/861; A61B 17/8615; A61B 17/862; A61B 17/8625; A61B 17/863; A61B 17/8635; A61B 17/864; A61B 17/8645; A61B 17/865; A61B 17/866; A61B 17/8685; A61B 34/10; A61B 2034/104; A61B 2034/105; A61B 2034/108
See application file for complete search history.

(56) References Cited

U.S. PATENT DOCUMENTS

| 7,799,057 | B2 * | 9/2010 | Hudgins | ............... A61F 2/4405 606/328 |
| 2007/0055236 | A1 * | 3/2007 | Hudgins | ............... A61F 2/4405 606/278 |
| 2020/0268449 | A1 * | 8/2020 | Solitro | .................. A61B 6/032 |
| 2021/0378752 | A1 * | 12/2021 | Paul | ...................... A61B 34/10 |
| 2022/0039868 | A1 * | 2/2022 | Chaoui | .................. A61B 5/743 |

\* cited by examiner

*Primary Examiner* — Eric S Gibson
(74) *Attorney, Agent, or Firm* — Jones Walker LLP

(57) ABSTRACT

A method of treating one of fractures and disfunctions of a pelvic ring of a patient comprising scanning a patient with a transdermal scan, determining, via a machine, from the scan an optimal range of angles of entry and sizes of screw to insert into the patient, communicating the optimal range to a surgeon, and inserting the screw into the patient.

16 Claims, 8 Drawing Sheets
(7 of 8 Drawing Sheet(s) Filed in Color)

TOOL AND METHOD TO EVALUATE SAFETY AND ANGULAR RANGES OF PINS AND SCREWS USED FOR PELVIC FIXATION

CROSS REFERENCE TO RELATED APPLICATIONS/PRIORITY

The present invention claims priority to U.S. Provisional Patent Application No. 62/809,183 filed Feb. 22, 2019, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND

Pelvic stabilization can be required when patients have a dysfunction of the pelvic ring and fractures that typically require fixation can be found in 20% of poly-trauma patients. Recently, the pelvic subcutaneous anterior internal fixation (INFIX) has been adopted as an alternative to external fixation, particularly in the obese population due to the increased amount of soft tissue in the pelvic region, including for emergency reduction of pelvic ring disruptions. Indications for this procedure include trans-symphysial instability with a gaping symphysis of greater than 2 cm and it is also adopted in combination with posterior fixation for treating rotationally and vertically unstable pelvic injuries. Benefits of the INFIX compared to pelvic external fixation are less soft tissue dissection, shortened operating time, no open pin tracts, ease of use in the obese population and superior stiffness. Reduction of anterior ring injuries are completed by compression or rod distraction before locking the rod into place with either mono or poly-axial pedicle screws.

There is a common consensus on the location of screw insertion which is identified in the center of the anatomical teardrop of the supraacetabular region on the anterior pelvis. Screw sizing is selected to maintain full intraosseous containment at the time of surgery and a wide range of diameters from 6.5 mm to 10 mm has been proven successful.

A wide range of screw lengths has also been reported by many authors but no specific criteria for its determination has been proposed. Ranges suggested are from 60 mm to 100 mm. Furthermore, others suggest the need for at least 60 mm of intraosseous screw containment and successfully adopted screw lengths from 75 mm to 150 mm based on the habitus of the patient. Complications of this technique occur from the screws and connecting bar being inserted too deep.

Also, it is important to obtain screw containment and avoid posterior cortex breaching at the angles of insertion. With exemption of Vaidya et al. that suggested drilling of the screw, in the direction of the posterior superior iliac spine just above the sciatic notch, in existing literature, screw angulation is often not disclosed. When it is disclosed it is not supported by a criterion for its determination at time of surgery. It is also highlighted that this technique has a learning curve associated with the depth placement of the screws and connecting rod. While there is a common consensus on the locations of screw insertion, there is a wide range of screw lengths and angulations have been reported by many authors without specific criteria for their determination. Such elements are arbitrarily decided at time of surgery with fluoroscopic verification of intraosseous placement. All of this leads to a potential significant risk of complication and harm to the patient under current technology. There are no systems assisting surgeons in selection and placement of screws or pin in the pelvic bone. Adoption of such system could reduce operating time, and minimize the risk of the implantation and simplify the process

SUMMARY

Wherefore, it is an object of the present invention to overcome the above-mentioned shortcomings and drawbacks associated with the current technology.

The disclosed invention relates to devices and methods of treating one of fractures and disfunctions of a pelvic ring of a patient comprising scanning a patient with a transdermal scan, determining, via a machine, from the scan an optimal range of angles of entry and sizes of screw to insert into the patient, communicating the optimal range to a surgeon, and inserting the screw into the patient. According to a further embodiment, the angles are transverse and sagittal angles. According to a further embodiment, the size of the screw is a length of between 60 mm and 150 mm. According to a further embodiment, the transdermal scan is one of a CT scan, an MRI, and an X-ray. According to a further embodiment, the optimal ranges are determined by drawing on a cross section of the patient's pelvis a pattern of screws in given angulations and lengths and query a system of artificial intelligence to indicate the containment. According to a further embodiment, the optimal ranges are determined by each screw 2d section being discretized in bitmap and full containment is given for the screws having all the bitmaps intersecting all bitmap representing a pelvic bone. According to a further embodiment, the optimal ranges are determined by lines being drawn from an entry point at different angles in a section plane to harvest at given intervals along a line bone density values. According to a further embodiment, the method includes density values being harvested on a left and right of the line at a distance that is equivalent to an outer radius of the screw, and positions along the line at which values are below a certain threshold giving an intraosseous distance, and screw containment along a direction of the line being ensured when the measured intraosseous distance is greater than the screw length. According to a further embodiment, the method includes transverse and sagittal inclinations being given to the surgeon as angles to insert the screw into the patient, and inserting the screw into the patient based on such inclinations. According to a further embodiment, the method includes the machine calculating an outlet location in relation to recognizable landmarks, and the inserting the screws into the patient based on the outlet location. According to a further embodiment, the method includes displaying optimal ranges on one of on a screen, or in augmented reality, and the surgeon inserting the screws into the patient while watching such display. According to a further embodiment, the method includes optimal ranges are given to guide an orientation of a drilling guide actuated by a robotic arm, and the screw is inserted into the patient based on the drilling guide. According to a further embodiment, the method includes optimal ranges are indicated to the surgeon with haptic, audible, visual feedbacks or some combination thereof, via the machine, while a surgical tool is been oriented at time of drilling, with the feedback indicating desired location and angles of drilling. According to a further embodiment, the method includes generating a 3D printed template incorporating an outlet location, and using the 3D printed template to insert a screw into a patient. According to a further embodiment, the method includes shaping a drilling guide, based on optimal range, such that when the drilling guide is matched with a pelvic bone surface at a tunnel entry point, an orientation is elaborated for the surgeon, using the drilling guide to insert a screw into a patient. According to a further embodiment, the machine includes a processor, a non-volatile memory storing instructions, an input, an output, a wireless transmitter and receiver, a bus, and a plurality of sensors.

The disclosed invention relates a method to process imaging data and tools that can be used to insert screws along evaluated safe trajectories.

The disclosed invention relates to computer assisted orthopedic surgery.

The disclosed invention relates to software, tools, and/or robotic systems that can assist the surgeon in the fixation of pelvic bone.

The disclosed invention relates to the surgical stabilization of the pelvic ring.

The disclosed invention relates to new guidelines for INFIX screw insertion in the transverse and sagittal planes and determine how ranges of angulation are associated with different screw intraosseous depths.

The disclosed invention relates to methods that can be used at time of surgical planning to evaluate full bone containment of screws or pins, considering diameter, intraosseous depth, inclinations in the sagittal and transverse anatomical planes and of tools to facilitate the screw insertion.

The disclosed invention relates to methods and devices to indicate to the surgeon differences in angular ranges in relation to screw diameter and intraosseous depths.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of the specification, illustrate various embodiments of the invention and together with the general description of the invention given above and the detailed description of the drawings given below, serve to explain the principles of the invention. It is to be appreciated that while the accompanying drawings are to scale, the emphasis is instead placed on illustrating the principles of the invention. The invention will now be described, by way of example, with reference to the accompanying drawings in which.

DETAILED DESCRIPTION

Figure 1:
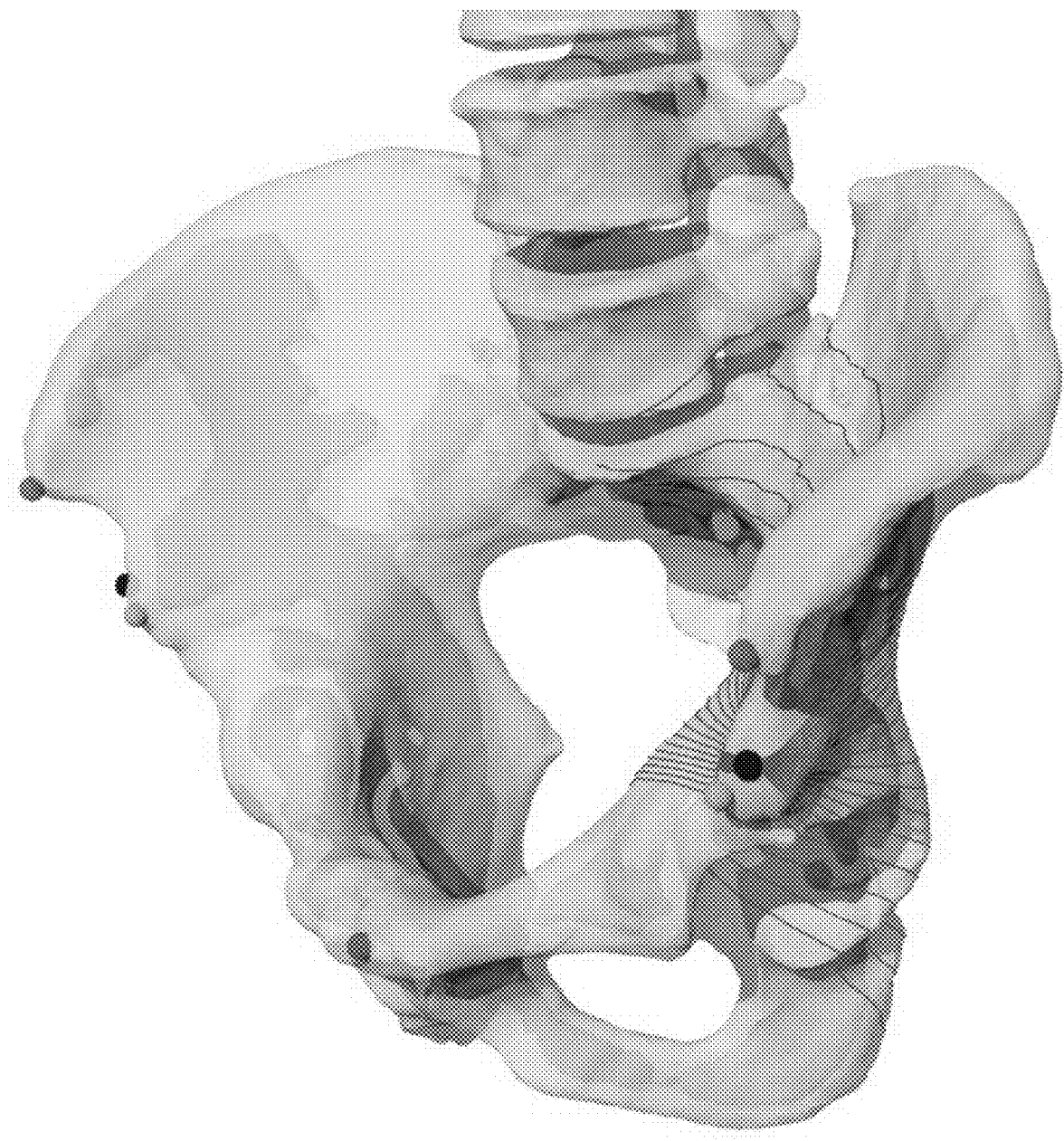
FIG. 1 is a tridimensional pelvis reconstruction showing the landmarks indicated by the surgeon: points of insertion (blue), AIISs (yellow), ASISs and left pubic tubercle (red) used to identify the anterior pelvic plane.

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1-8B, a brief description concerning the various components of the present invention will now be briefly discussed.

Three-dimensional reconstructions were obtained from CT scans and a computer algorithm created cross-sections at sagittal inclinations ranging from 45° cranial to 45° caudal in 5° increments. Templates of screws with depths spanning 60 to 120 mm in increments of 15 mm were disposed in the transverse plane from 45° medial to 45° lateral. Each depth and transverse angle were evaluated for interosseous containment. Differences in sagittal ranges were evaluated for consecutive lengths and normality.

Inclinations greater than 30° caudally were not feasible along with depths above 75 mm in caudal inclinations greater than 5°. The 60 mm depth resulted in the largest sagittal range of 60.9°±6.9 and transverse range of 27.5°±4.1° at 30° caudal. Bisecting angles were similar for sagittal planes 20° cranial to 30° caudal with an average of 27.9°±1.2° ($p \geq 0.115$). Increasing depths by 15 mm resulted in ranges being significantly different from one another ($p<0.01$). The sagittal plane of 20° cranial had the highest frequency of insertion for all depths while transverse ranges were narrowed ($p<0.01$).

The inventors created guidelines for insertion in relation to screw depth. While 60 mm depths can be inserted with the highest discretion, 15 mm increases significantly reduce safe ranges. Screws with depths above 90 mm should be inserted more cranially but are more prone to breaching. The identified ranges give indications on screw selection in relation to safety of implantation.

At surgery, the patient is in the supine position. A three-cm incision is performed bilaterally at the anterior inferior iliac spine (AIIS) and blunt dissection is taken down to the location of pedicle screw placement. The connecting rod is pre-contoured to the patient and inserted subcutaneously to run across the pelvic region in the "bikini line" (see FIGS. 4 and 5). Placement of the rod in this area avoids neurovascular and muscular impingement, allowing patient to sit or achieve a squatting position. Caution must be taken to avoid damage to the lateral femoral cutaneous nerve which usually runs across the surgical field.

Because, in existing literature there are no clear indications on how angulation and screw length should be determined at the time of surgery planning, the inventors aimed to create algorithms for INFIX safe screw insertion in the transverse and sagittal planes, as well as include how these safe ranges of angulation are associated with different screw lengths to reduce this learning curve. The inventors also investigated the relationship between anatomical size of the pelvis and screw size. The inventors hypothesized that such criteria for screw selection and insertion can be drawn from a clinical dataset and a short screw can be inserted with high discretion. The inventors also expect this range to be affected by an increase in screw length.

The disclosed method includes the elaboration with the following steps of imaging data obtained preferably by CT scan.

Landmarks to establish anatomical planes and insertion points are indicated by the surgeon. In the inventors' experience, the inventors have found easy identification of the anterior superior iliac spine (ASIS) on the left and right sides along with the left pubic tubercle (see FIG. 1). The plane containing these three points is indicated as anterior pelvic plane. The sagittal plane is drawn as the plane perpendicular to the line connecting the two ASIS and passing through the midpoint. The remaining transverse plane is drawn as the plane containing the line connecting the two ASIS and perpendicular to the anterior pelvic plane.

The sagittal plane is used to identify the two pelvis hemipelvises that are individually analyzed. For each hemipelvis, the planes parallel to the transverse plane but passing through the indicated entry point are rotated of a given angle (5 deg) around the axis parallel to the line connecting the two ASIS and passing through the entry point (see FIG. 2a). The profiles obtained from the intersection between the bone and these planes are used to evaluate bone containment of the screws.

Figure 2B:
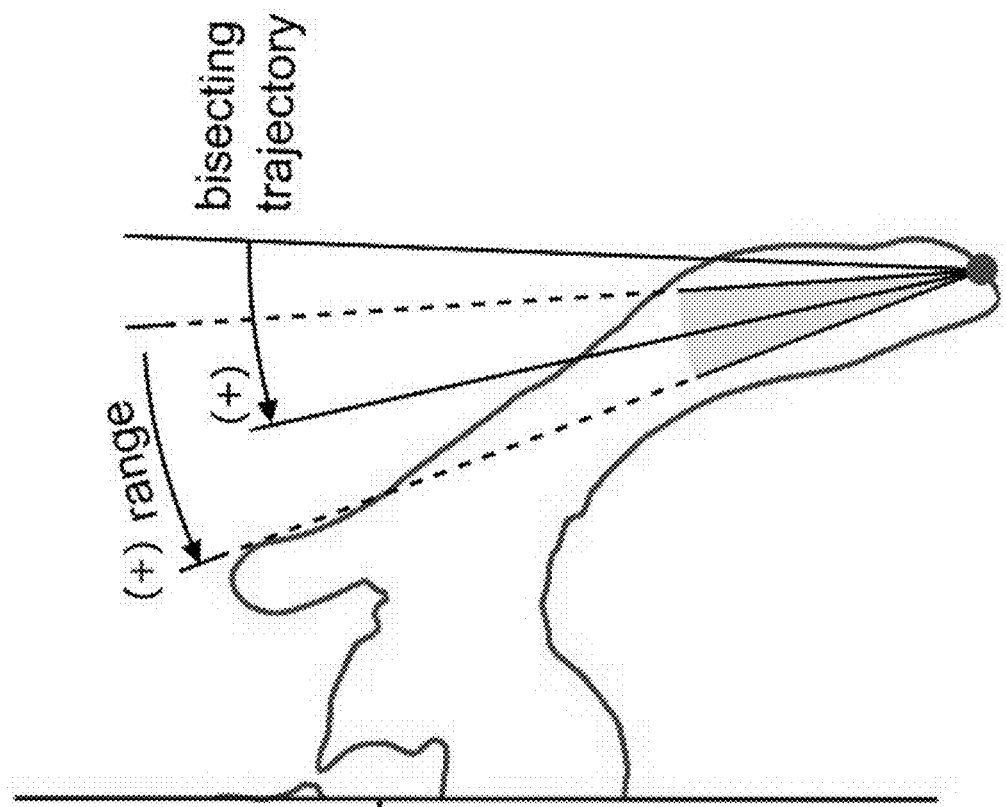
FIGS. 2A and 2B are lateral view of the sectioning in the sagittal plane from 45° cranial to 45° caudal (a) and one of the transverse sections in which the bisecting trajectory and safe range are highlighted for a 75 mm ISD (b).

It must be noted that this intersection can be performed in several manners in relation to the data available. Having CT data, each planar section can be obtained interpolating the HU values of the voxels intersecting the plane or for interpolation of the HU values of the voxels surrounding the plane. In the other case that a tridimensional reconstruction of the bone is already available, the planar section is obtained as the intersection between the 3D geometry and the plane as shown in FIG. 2b.

Evaluation of full bone containment in each plane can also be performed in several manners.

A first manner would be to draw on the cross section a pattern of screws in given angulations and lengths and ask a user or a system of artificial intelligence to indicate the containment.

In a second manner, each screw 2d section is discretized in bitmap and full containment is given for the screws having all the bitmaps intersecting all the bitmap representing the bone.

In a third manner, from the entry point lines at different angles are drawn in the section plane to harvest at given intervals along the line bone density values. More specifically the density values are harvested on the left and right of the line at a distance that is equivalent to the screw outer radius. The positions along the line at which the values are below a certain threshold gives the intraosseous distance. Screw containment along the direction of the line is ensured when the measured intraosseous distance is greater than the screw length.

An Example of the application of the described method for subcutaneous anterior fixation can be found below.

Figure 3:
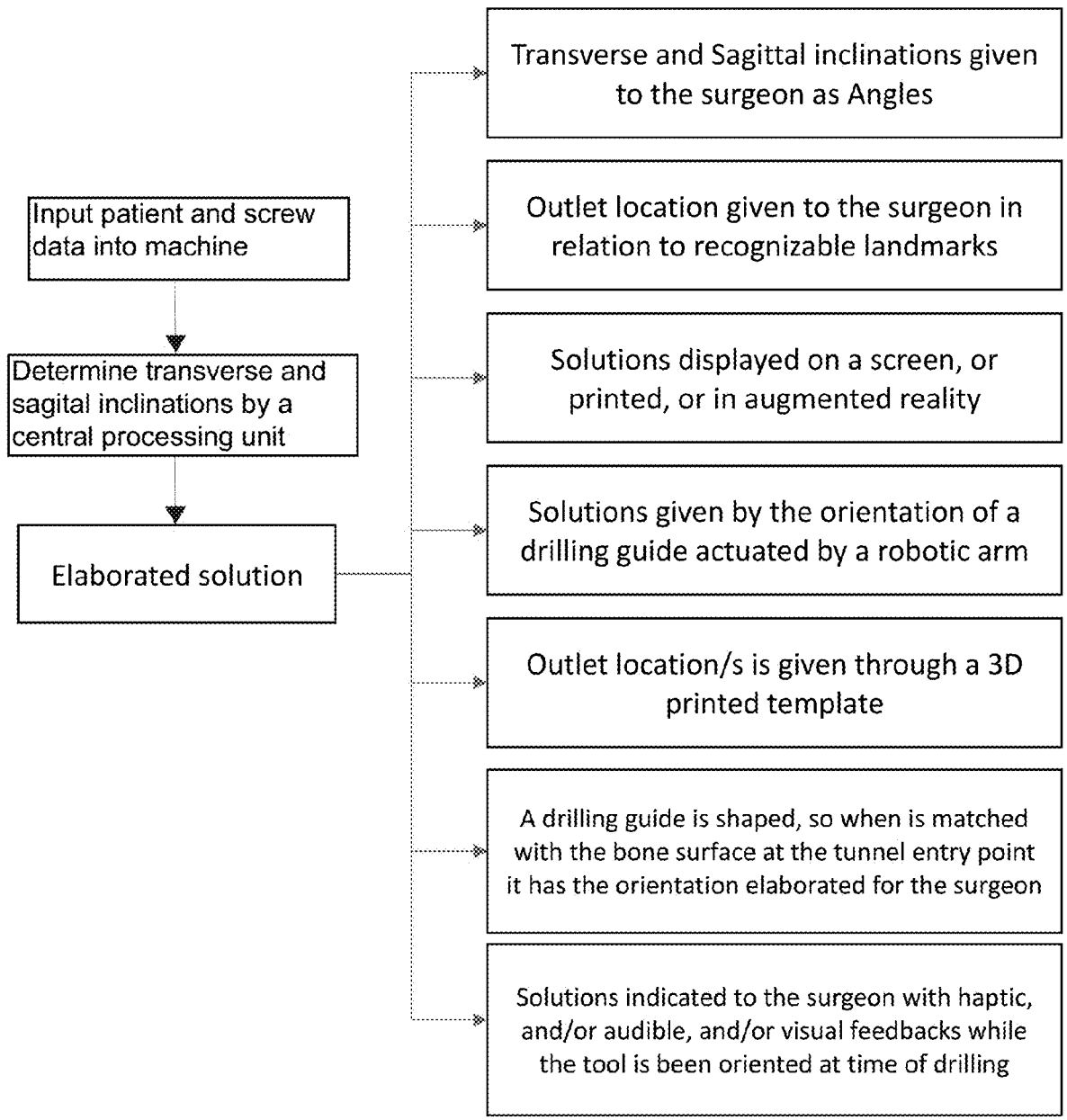
FIG. 3 is a flow chart of various embodiments of the method of using the disclosed invention.

The proposed method can be used with several existing technologies to obtain surgical tools, as shown in FIG. 3.

Patients and Methods

Materials and Patients

Computer tomography (CT) data from a single level 1 trauma center was acquired from February 2012 to February 2018. Ages 18-70 were selected due to this population being more prone to pelvic fractures in need of fixation and to avoid the use of pediatric patients. Intact pelvises were identified using the following exclusion criteria: acetabular column fractures, ilium fractures, previous pelvis surgery with retained hardware, and poor-quality scans after segmentation. A total of 86 CT scans were used having a slice thickness of 1.5 mm and an in-plane pixel size of 0.568 mm.

Methods

Each CT scan was segmented into a 3D model using InVesalius software utilizing threshold values characteristic of human bone and isolating pelvic bones comprehensive of the sacrum. The obtained models were then imported into AutoDesk MeshMixer (AutoDesk Inc., San Rafael, Calif.) to remove cavities still remaining after segmentation and smooth the surface. The solid accuracy and mesh density settings were set to 1.5 mm. The 3D reconstruction was exported as an STL file into Rhinoceros 3D (Robert McNeal, Seattle, Wash.) for further processing. A surgeon trained in internal fixation identified the anterior superior iliac spine (ASIS) on the left and right sides along with the left pubic tubercle. These landmarks were identified to form an inverted triangle which was designated as the anterior pelvic plane. The origin of the plane was set in the middle between the two reference points of the left and right ASISs. The transverse plane was set perpendicular to the identified anterior pelvic plane and passed through both ASIS regions (see FIG. 1).

Screw insertion points in the center of the anatomical teardrop of the supraacetabular region and the anterior inferior iliac spines (AIIS) were set on both the left and right sides.

Figure 2A:
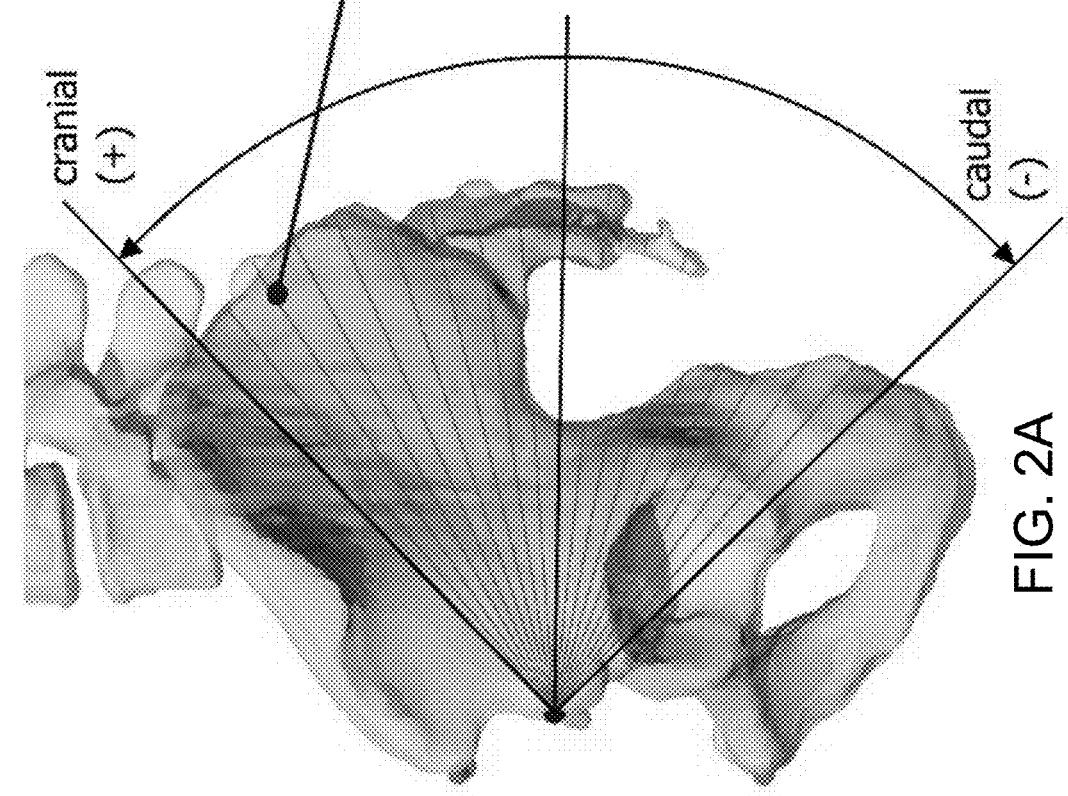

A custom-built algorithm was used to create cross-sections that were drawn at sagittal inclinations ranging from 45° cranial to 45° caudal in 5° increments (see FIG. 2A). This resulted in the display of 19 different cross sections of the pelvis corresponding to the different sagittal planes. At each cross section of the sagittal planes, a template of pedicle screws with intraosseous screw depths (ISD) spanning from 60 mm to 120 mm in increments of 15 mm were created in the transverse planes from 45° medial (positive) to 45° lateral (negative). The ISD of 120 mm was selected corresponding to longest documented screw length of 150 mm. The screw length was considered as the sum of the intraosseous depth and 15 mm distance that has been suggested as gap between the bone and screw head to avoid impingement with soft tissues. The screw core diameter of the template was set to 4 mm as representative to a screw size of 6.5 mm.

Methods of Assessment

The created algorithm measured distances between the left and right ASIS, the ASIS and AIIS, the ASIS and screw entry, AIIS and screw entry, and left pubic tubercle to the left and right ASIS. For each ISD, the inventors evaluated the ranges of sagittal and transverse inclination where the screw core was fully contained in the bone cross section. As an additional conservative measure to avoid invasion of the acetabulum, the inventors did not consider as safe the screws that were fully contained in the bone, but within 10° of sagittal inclination from the observed acetabulum apex.

The transverse safe range for each sagittal angle was determined by finding the difference between the maximum and the minimum feasible angles (see FIG. 2B). After identifying the safe transverse range, the inventors found the average bisecting angle in the transverse plane for each sagittal angle that can be considered as the ideal trajectory for that plane.

To associate pelvis size with feasibility of the 120 mm ISD, the inventors divided the specimens into two groups, isolating specimens in which a sagittal range greater than or equal to 15° was feasible. In the group allowing insertion with this sagittal range, the inventors then further isolated and compared pelvises that allowed insertion with transverse ranges greater than or equal to 5° in the 15° sagittal range.

Statistical Analysis

Angular ranges were evaluated for normality using the Shapiro Wilk test. Sagittal angles at which screw depths could be inserted with similar transverse angles were identified performing a Kruskal Wallis test of the bisecting angle. Differences in safe sagittal ranges and bisecting angles were evaluated for consecutive ISDs of 60-75 mm, 75-90 mm, 90-105 mm, and 105-120 mm using the Wilcoxon test. The equivalence in pelvis dimensions between pelvises with feasible 120 mm ISDs were identified using the Wilcoxon test. The level of significance for all tests was set to 0.05.

Results

The left and right sides of each pelvis had similar measurements between the ASISs and AIISs (p=0.830). The distance between the left and right ASISs was found to be 225.1 mm±19.3 mm while the distance between the ASIS and AIIS was 40.0 mm±5.6 mm. Insertion resulted as just superior and slightly lateral to the AIISs with distances of 33.0 mm±5.4 mm and 9.0 mm±2.1 mm, respectively, from the ASIS and the AIIS. All screw insertion depths hypothesized were feasible in 99.1% of the analyzed specimens with at least one combination of sagittal and transverse angles. The ISD values showed no difference between the left and right sides in sagittal range (p≥0.235). Using a paired comparison, each insertion depth (see FIG. 6) was found to be significantly different from the subsequent (see, p<0.01).

TABLE 1

| Sagittal Ranges of Screw Depths [deg] | | | | | | |
|---|---|---|---|---|---|---|
| Side: | | 60 mm | 75 mm | 90 mm | 105 mm | 120 mm |
| Right | Avg | 60.9 | 47.5 | 25.9 | 22.7 | 19.1 |
| | St Dev | 6.9 | 12.1 | 6.7 | 6.7 | 7.6 |
| Left | Avg | 60.4 | 48.0 | 26.0 | 22.1 | 19.4 |
| | St Dev | 6.4 | 13.8 | 8.5 | 7.5 | 7.7 |
| | P-Value comparing Left vs Right | 0.539 | 0.874 | 0.959 | 0.235 | 0.760 |
| Combined | Avg | 60.7 | 47.8 | 25.9 | 22.4 | 19.5 |
| | St Dev | 6.6 | 12.9 | 7.6 | 7.1 | 7.7 |

Average Sagittal Ranges for Right, Left, and Combined Sides Including Standard Deviation and p Values At 30° caudal the inventors found the largest transverse range of 27.5°±4.1° for the 60 mm depth (p=0.038) and 12.5°±9.1° for the 75 mm depth (see FIGS. 7A and 7B, and FIGS. 8A-8C). However, insertion in this plane was feasible for only 3.6% of specimens.

The percentage of specimens allowing 60 mm of ISD varied in relation to the considered sagittal plane and ranged from 96.4% at 5° caudally to 6.25% for the plane at 25° caudally. (see FIGS. 8A-8C Error! Reference source not found.). In the sagittal range of 30° cranial to 0°, the inventors found that almost 100% of specimens allowed for insertion of the 60 mm ISD and had the highest frequency for all other depths. At 20° cranial, 100% of our specimens allowed for safe insertion up to the ISD of 90 mm and the 120 mm depth had the highest frequency of insertion of 83.9% in this plane. Transverse ranges were compared here for each depth and all were found to be significantly narrowed (p<0.01, see Error! Reference source not found.). Using the 60 mm ISD, the transverse range in the sagittal planes of 20°, 25°, and 30° cranial were found significantly different (p<0.01).

TABLE 2

| Average Transverse Range at 20° Cranial | | | | | |
| --- | --- | --- | --- | --- | --- |
|  | 60 mm | 75 mm | 90 mm | 105 mm | 120 mm |
| Avg Range: | 14.1° | 10.5° | 9.2° | 7.3° | 5.7° |
| St. Dev: | 4.4° | 4.1° | 4.0° | 3.3° | 2.8° |

Average Transverse Range and Standard Deviation for Each ISD at 20° Cranial. This table proves the decrease in transverse ranges between each increase in screw depth We found the bisecting angles with an average of 27.9°±1.2° were similar for all ISDs from 20° cranial to 30° caudal (p≥0.115). In this range, inclinations greater than 0° caudally were not feasibly safe for all ISDs greater than 75 mm.

83.0% of specimens allowed for the insertion of 120 mm ISD in at least a 15° sagittal range with an average of pelvic width of 225.2 mm±19.5 mm. Of those, insertion in sagittal planes with transverse ranges of 5° or more resulted in 28.6% specimens having an average pelvic width of 227.6 mm±20.2 mm. No significant difference was found between anatomical dimensions in pelvises that were or were not able to accommodate the 120 mm ISD in the 15° range (p=0.880) or in the 15° range with a transverse range greater than 5° (p=0.406). Within the sagittal range of 15° to 25° cranially, 61.6% of specimens were able to safely have a 120 mm ISD inserted with an average pelvic width of 224.6 mm±19.7 mm. No statistical difference was found between anatomical sizing of pelvises that could or could not insert a 120 mm ISD within this range (p=0.946).

Figure 4:
FIG. 4 is a Blunt dissection for subcutaneous anterior internal fixation (INFIX) (a).
Figure 5:
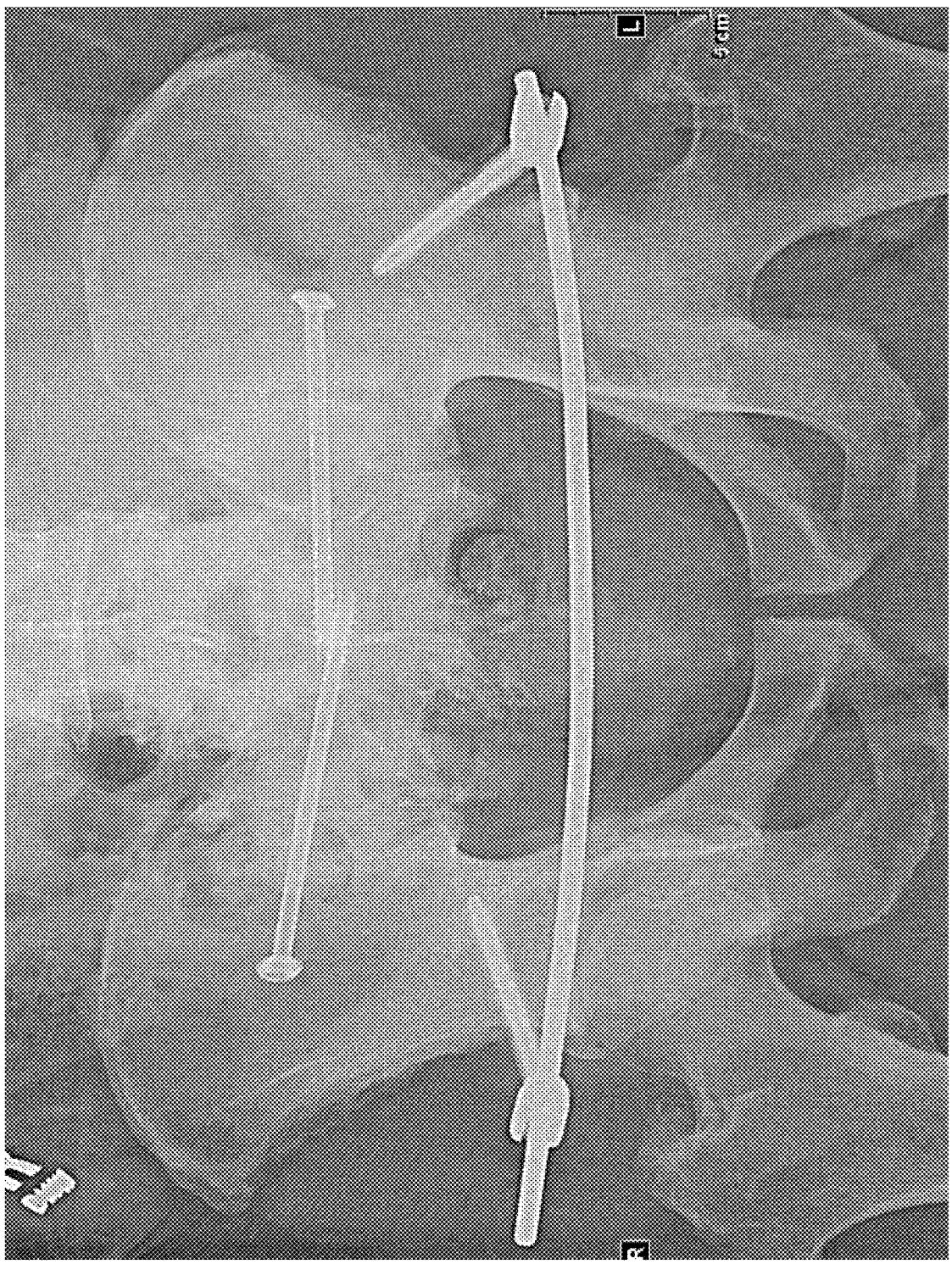
FIG. 5 is an x-ray image of the subcutaneous anterior internal fixation of FIG. 4, showing asymmetric screw insertions.
Figure 6:
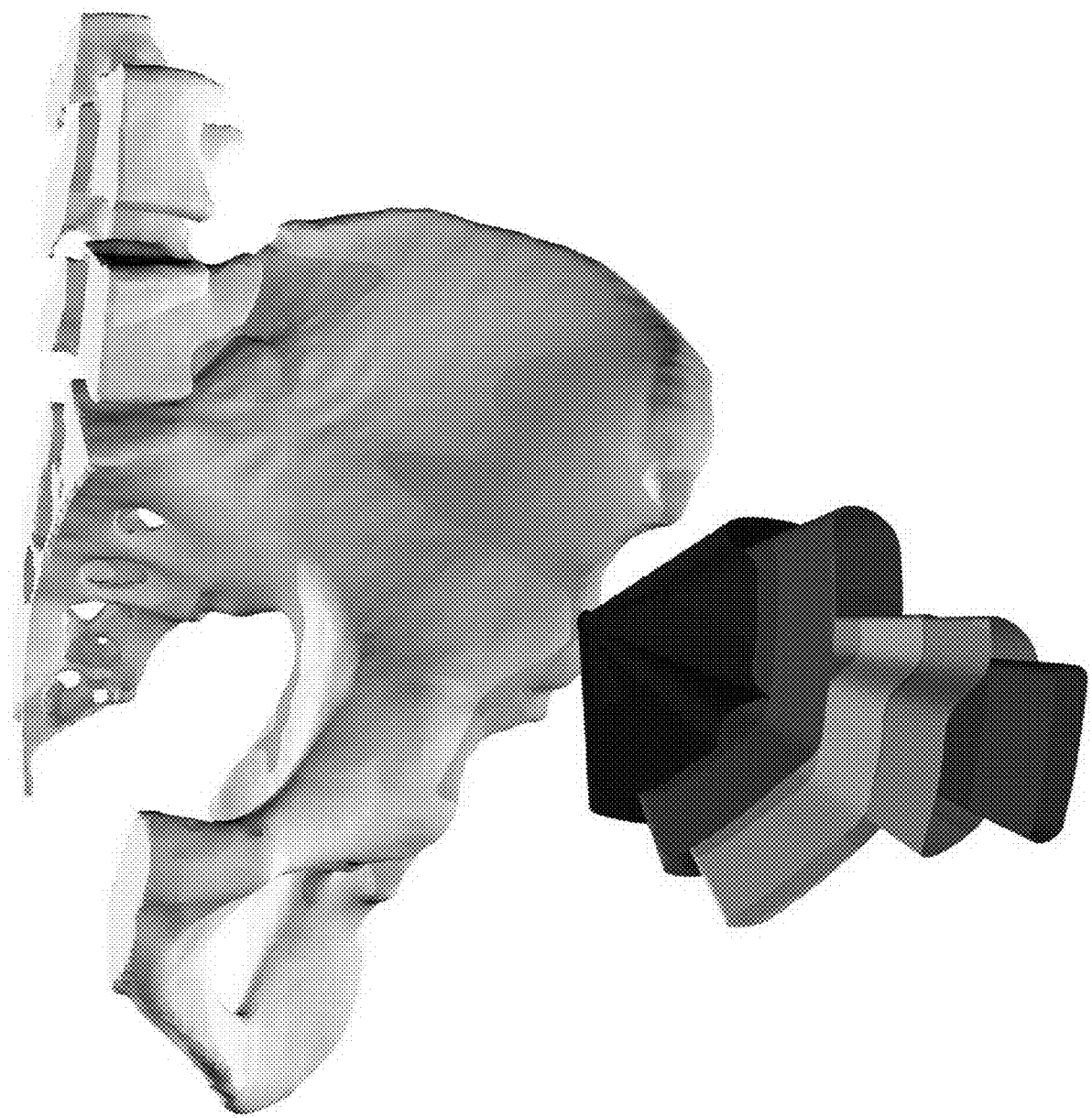
FIG. 6 is a three-dimensional representation of results showing safe angulation of insertion for the 60 mm (blue), 75 mm (green), 90 mm (yellow), 105 mm (orange), and 120 mm (red) depths in sagittal and transverse planes.
Figures 7A, 7B:
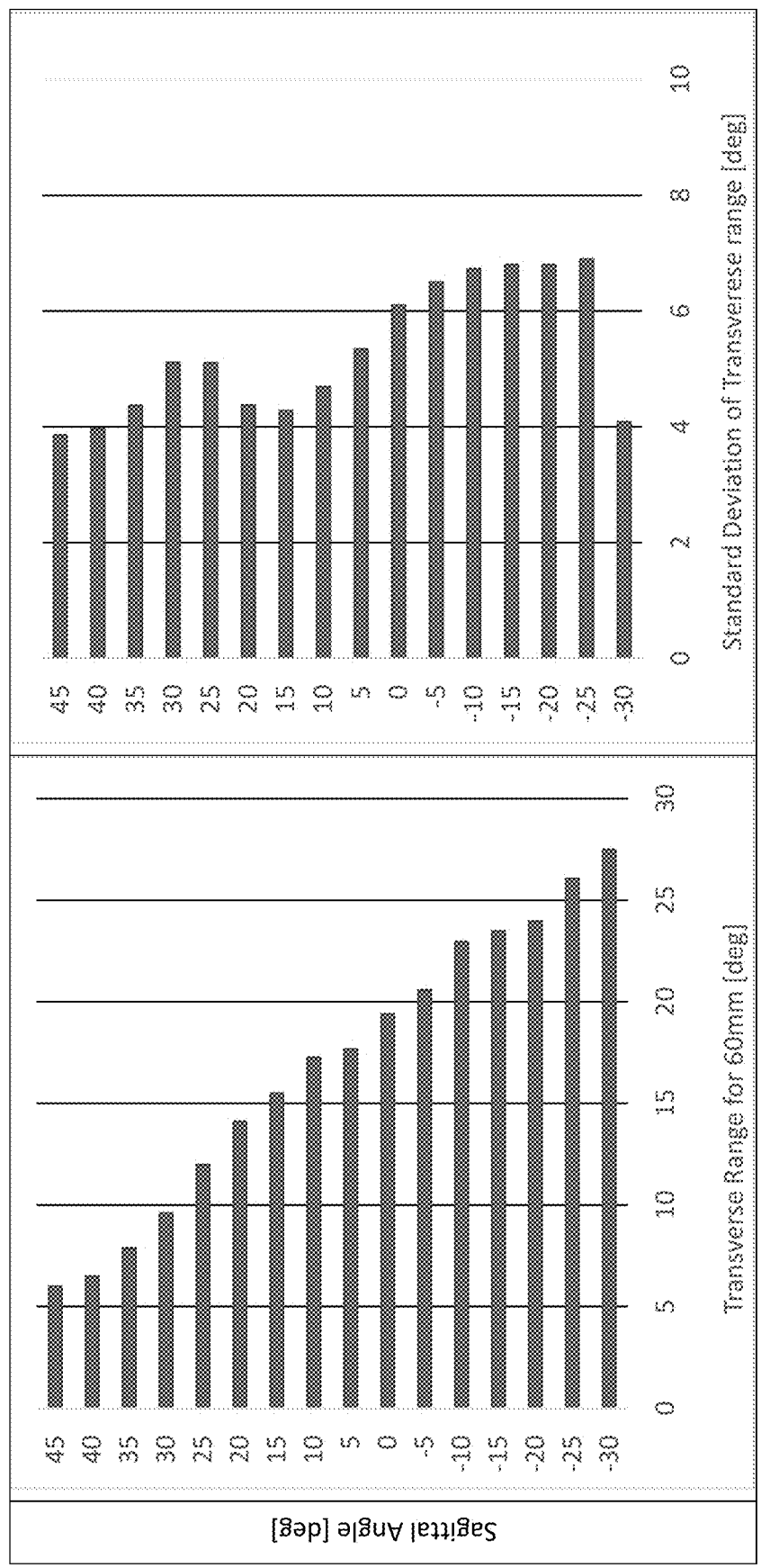
FIGS. 7A and 7B are graphs depicting the transverse range and standard deviation for the 60 mm ISD at each sagittal plane from 30° caudal to 45° cranial. As the sagittal plane extends caudally, an increase in the safe transverse range can be seen.
Figures 8A, 8B, 8C:
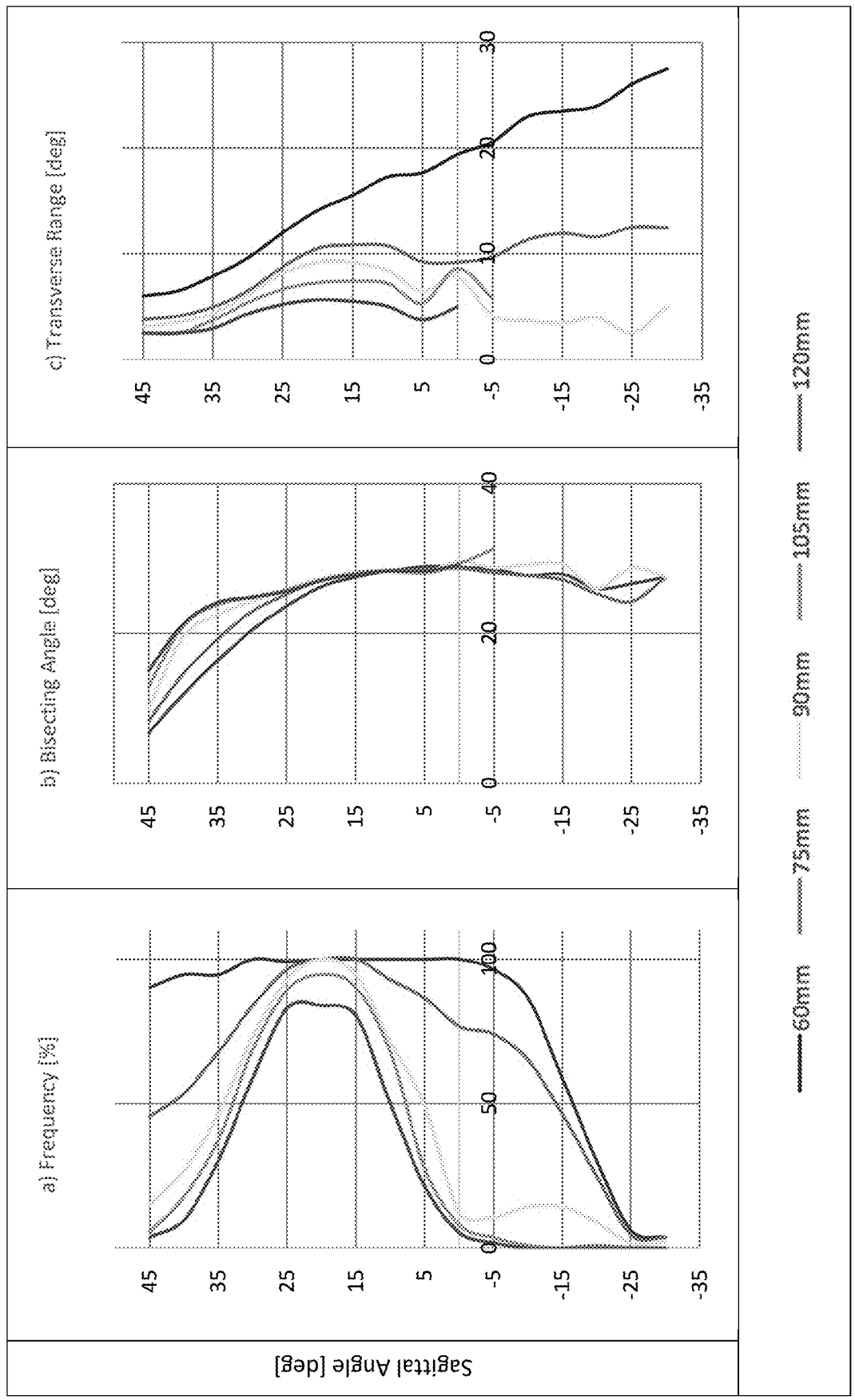
FIGS. 8A to 8C are graphs depicting the frequency of insertion for sagittal angles 30° caudal to 45° cranial (a), Graph showing average bisecting angles for each sagittal plane (b), Graph displaying the transverse.

This study was designed to determine the safe range of screw insertion in the supraacetabular region for INFIX. Proper selection of these angles is essential to avoid breaching the pelvic wall and maintain full intraosseous containment. Safe transverse ranges increased caudally with values ranging from 6.0°±3.9° to 27.5°±4.1° for a 60 mm ISD. However, not all screw depths can be safely inserted into all patients. The inventors determined 5° to 30° in the caudal direction resulted in large ranges in the transverse plane that was only feasible for ISDs of 60 mm and 75 mm. From 20° cranial to 30° caudal the inventors found that all ISDs were feasible with an average bisecting angle of 27.9°±1.2° (p≥0.115). Increasing ISD strongly narrows the safe transverse range (p<0.01) with a minimum of 2.5° range for the 120 mm ISD. This value is smaller than what has been previously indicated as surgeon accuracy for screw insertion at 4.3° of median error. Vaidya et al. indicated screw selection based on the habitus of the patient to avoid breaching, but for the longest ISD the inventors found no differences between body habitus. Bone morphology was found to be more relevant than body habitus even if the inventors did not numerically estimate morphological features. Previous literature has suggested the supraacetabular region as an optimal location for screw insertion for temporizing pelvic fixation. Utilizing the supraacetabular insertion point provides the widest ranges of insertion and the greatest stability biomechanically. Our study found that this area corresponds to the highest percentages of safe insertions with peaks of frequencies at 20° cranial for all ISDs. In this area, the 60 mm insertion could be achieved with high discretion in transverse ranges. The inventors found that the 60 mm screw depth provided the best option to limit breaching of the pelvic wall having the largest ranges in both transverse and sagittal directions. In the cranio-caudal direction, the pelvis has a slight "S" shape that varies among individuals from almost straight to angles of approximately 60° in curvature proving the irregularities in safe range as shown in FIG. 4. The inventors observed the depth of the pelvis in the anteroposterior direction to be shallower in more caudal planes. Anatomically, these findings correlate to the greater sciatic notch where the pelvis curves anteriorly. Here, care must be taken to avoid a breaching injury to the neurovascular and musculature passing through the foramen. Because insertion into the acetabulum is considered a major complication, the inventors determined in all our specimens that insertion of screws greater than 5° in the caudal direction was unacceptable. Scheyerer et al. stated to aim 20° in the cranio-caudal direction, but the inventors found this sagittal inclination only in 30.4% of the subject when using a 60 mm ISD.

The main limitation of the study should be found on the fact that all the measures the inventors performed are based on entry point established by a surgeon and the inventors did not evaluate the sensitivity of our results to the variation of such entry point. However, the chosen point is largely documented in literature and it is of easy identification, that is performed without bias. This study used intact pelvises for reconstruction. At the time of surgery, variations in open pelvises will result in distorted anterior pelvic planes, leading to a wide range of orientation in the transverse and sagittal planes. Other studies also used intact pelvises and further studies should be dedicated to translate the angulations found in the pelvic reference frame to hemi pelvic specific planes. In similarity of previous studies, the inventors based our measures on tridimensional reconstructions not specifically performed for scientific research; however, our results are directly usable for clinical practice. Another limitation is represented by the adoption of radiographic CT scans in place of cadaveric specimens. Having a large sample size, it was more feasible to analyze these angles of insertion using computer simulations that allowed the sagittal and transverse angles to be displayed at once. In each hemi pelvis, the inventors analyzed 19 transverse angles at 19 sagittal inclination for five insertion depths for a total of 1805 insertions. However, cadaveric validations of our ranges can be tested for further investigation. Lastly, the inventors focused on only one screw diameter. Because our algorithm was not fully automated, the inventors had to limit the screw dimension to the most commonly adopted. Reports of using larger diameter screws, such as 7 mm, resulted in insertion difficulty for patients that do not have a broad width in their AIIS. The sagittal ranges were significantly narrowed between increases in screw depths and exemplified that with a 15 mm increase, the feasibility of keeping the screw intraosseously contained was more difficult. It was determined that longer screw depths were possible if they were directed in a caudo-cranial direction, usually above 5° cranial due to the anatomical characteristics of the pelvis. The inventors deduce surgeon experience and overcoming the learning curve may play a large part for correct insertion of longer screw depths. There were limitations to how the inventors explored the narrowing range with increasing screw depth as well. The inventors used 15 mm increments in length and 5° increments in the sagittal and transverse angles. The inventors understand that these increments may not be commercially available for use in practice. With keeping 15 mm increments, the inventors were able to have a compromise between different screw sizes and a reduction in the number of configurations ranging from documented sizes of 60 mm to 110 mm. The inventors also did not account for the conical shape of the screw and the inventors opted for more conservative results considering a constant screw cross section. For future development of this study, an algorithm with the ability to evaluate all feasible trajectories for other angles should be further explored.

In conclusion, the inventors disclose feasible trajectories for longer screw lengths (>75 mm), and provide precise safe corridors in relation to screw lengths. While the 60 mm screw can be safely inserted with highest discretion, a 15 mm increase significantly reduces this safe range. With possible complications that come with placing a screw too far in caudal sagittal planes, the inventors recommend insertion at 5° caudally considering the widest transverse range when a 60 mm insertion depth is desired, while the inventors suggest 20° cranially when discretion tolerance in transverse inclination is secondary to insertion depth. In this second case, longer screws are feasible with a small corridor of safety in the ilium. The identified ranges from this study give precise indications on safe screw insertion, giving the surgeon a tool for screw selection in relation to the safety of implantation. Such indications constitute a definitive guide for safe supraacetabular screw placement for the expert and novice surgeon alike.

In further embodiments, data can be imputed into a machine, an algorithm based on the disclosed invention can be run, and the outcomes can be applied to various therapeutic results. In one embodiment Transverse and Sagittal inclinations can be given to the surgeon as angles to insert the screw into the patient, and then the surgeon inserts the screw into the patient based on such inclinations. In a second embodiment, an outlet location is given to the surgeon in relation to recognizable landmarks, and the surgeon inserts the screws based on the outlet location. In a third embodiment, solutions are displayed on a screen, or printed, or in augmented reality, and the surgeon inserts the screws into the patient based on such display. In a fourth embodiment, solutions are given to guide the orientation of a drilling guide actuated by a robotic arm, and a screw is inserted into the patient based on the drilling guide. In a fifth embodiment, solutions are indicated to the surgeon with haptic, and/or audible, and/or visual feedbacks via the machine while the surgical tool is been oriented at time of drilling, with the feedback indicating the desired location and angles of drilling. In a sixth embodiment, the outlet location/s is given through a 3D printed template, which a surgeon uses to insert a screw into a patient. In a seventh embodiment, a drilling guide is shaped, so when is matched with the bone surface at the tunnel entry point it has the orientation elaborated for the surgeon, and the surgeon uses the guide to insert a screw into a patient. The machine would preferably have a processor, non-volatile memory, input, output, wireless transmitter and receiver, bus, and sensors, and be programmed to carry out the disclosed processes.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:

1. A method of treating one of fractures and disfunctions of a pelvic ring of a patient comprising:
   scanning a patient with a transdermal scan;
   determining, via a machine, from the scan an optimal range of angles of entry and sizes of a screw to insert into the patient;
   communicating the optimal range to a surgeon; and
   inserting the screw into the patient.

2. The method of claim 1 wherein the angles are transverse and sagittal angles.

3. The method of claim 1 wherein the size of the screw is a length of between 60 mm and 150 mm.

4. The method of claim 1 wherein the transdermal scan is one of a CT scan, an MRI, and an X-ray.

5. The method of claim 1 wherein the optimal ranges are determined by drawing on a cross section of the patient's pelvis a pattern of screws in given angulations and lengths and query a system of artificial intelligence to indicate a containment.

6. The method of claim 1 wherein the optimal ranges are determined by a screw 2d section being discretized in bitmap and full containment is given for the screws having all bitmaps intersecting all bitmap representing a pelvic bone.

7. The method of claim 1 wherein the optimal ranges are determined by lines being drawn from an entry point at different angles in a section plane to harvest at given intervals along a line bone density values.

8. The method of claim 7 further comprising density values being harvested on a left and right of the line at a distance that is equivalent to an outer radius of the screw, and positions along the line at which values are below a certain threshold giving a measured intraosseous distance, and screw containment along a direction of the line being ensured when the measured intraosseous distance is greater than a screw length.

9. The method of claim 1 further comprising transverse and sagittal inclinations being given to the surgeon as angles to insert the screw into the patient, and inserting the screw into the patient based on such inclinations.

10. The method of claim 1 further comprising the machine calculating an outlet location in relation to recognizable landmarks, and the inserting the screw into the patient based on the outlet location.

11. The method of claim 1 further comprising displaying optimal ranges one of a screen or in augmented reality, and the surgeon inserting the screw into the patient while watching such display.

12. The method of claim 1 further comprising optimal ranges are given to guide an orientation of a drilling guide actuated by a robotic arm, and the screw is inserted into the patient based on the drilling guide.

13. The method of claim 1 further comprising optimal ranges are indicated to the surgeon with haptic, audible, visual feedbacks or some combination thereof, via the machine, while a surgical tool is being oriented at a time of drilling, with the feedback indicating desired location and angles of drilling.

14. The method of claim 1 further comprising generating a 3D printed template incorporating an outlet location, and using the 3D printed template to insert the screw into the patient.

15. The method of claim 1 further comprising shaping a drilling guide, based on the optimal range, such that when the drilling guide is matched with a pelvic bone surface at a tunnel entry point, an orientation is elaborated for the surgeon, using the drilling guide to insert the screw into the patient.

16. The method of claim 1, wherein the machine includes a processor, a non-volatile memory storing instructions, an input, an output, a wireless transmitter and receiver, a bus, and a plurality of sensors.

* * * * *